United States Patent [19]
Tanabe et al.

[11] Patent Number: 5,274,150
[45] Date of Patent: Dec. 28, 1993

[54] PROCESS FOR PRODUCING 3,5-DI(α-METHYLBENZYL)SALICYCLIC ACID DERIVATIVE, AND USE OF POLYVALENT-METAL-MODIFIED PRODUCT THEREOF AS COLOR DEVELOPER

[75] Inventors: Yoshimitsu Tanabe, Yokohama; Keizaburo Yamaguchi, Chiba; Akihiro Yamaguchi, Kamakura, all of Japan

[73] Assignee: Mitsui Toatsu Chemicals, Incorporated, Tokyo, Japan

[21] Appl. No.: 740,386

[22] Filed: Aug. 5, 1991

[30] Foreign Application Priority Data

Aug. 6, 1990 [JP] Japan .................. 2-206711

[51] Int. Cl.$^5$ .................. C07F 3/06; C07C 65/10
[52] U.S. Cl. .................. 556/132; 556/27; 556/106; 556/115; 556/147; 560/57; 562/468
[58] Field of Search .................. 560/57; 562/468; 556/27, 106, 115, 132, 147

[56] References Cited

U.S. PATENT DOCUMENTS

| | | | |
|---|---|---|---|
| 4,745,203 | 5/1988 | Nachbur | 556/132 X |
| 4,748,259 | 5/1988 | Nachbur | 556/132 |
| 4,754,063 | 6/1988 | Nachbur | 562/468 |
| 4,879,368 | 11/1989 | Botta et al. | 528/397 |
| 4,952,648 | 8/1990 | Yamaguchi et al. | 525/539 |

FOREIGN PATENT DOCUMENTS

| | | |
|---|---|---|
| 0218553 | 4/1987 | European Pat. Off. . |
| 0219457 | 4/1987 | European Pat. Off. . |
| 0264051 | 4/1988 | European Pat. Off. . |
| 269619 | 7/1989 | Fed. Rep. of Germany . |
| 49-10856 | 3/1974 | Japan . |
| 61-26772 | 5/1986 | Japan . |
| 61-100493 | 5/1986 | Japan . |
| 62-96449 | 5/1987 | Japan . |
| 291042 | 9/1988 | Japan . |
| 1133780 | 9/1988 | Japan . |
| 2-91043 | 3/1990 | Japan . |

OTHER PUBLICATIONS

Chem. Abstracts, vol. 93, Aug. 18, 1980, 93:71304h.
Chem. Abstracts, vol. 79, No. 3, Jul. 23, 1973, 79:18310s.
English Abstract of JP-A-2091042 (1990).

*Primary Examiner*—Richard L. Raymond
*Attorney, Agent, or Firm*—Millen, White, Zelano, & Branigan

[57] ABSTRACT

A color-developing sheet using, as a color developer, polyvalent-metal-modified products of salicylic acid compounds composed mainly of a 3,5-di(α-methylbenzyl)salicylic acid derivative obtained by reacting a salicylic acid ester with an α-methylbenzyl halide in the presence of an acid catalyst and hydrolyzing the reaction product.

Said color-developing sheet has excellent color developability at low temperatures and gives a color of excellent water resistance.

15 Claims, 3 Drawing Sheets

PROCESS FOR PRODUCING 3,5-DI(α-METHYLBENZYL)SALICYCLIC ACID DERIVATIVE, AND USE OF POLYVALENT-METAL-MODIFIED PRODUCT THEREOF AS COLOR DEVELOPER

BACKGROUND OF THE INVENTION (1) Field of the Invention

The present invention relates to a novel process for producing a 3,5-di(α-methylbenzyl)salicylic acid derivative useful as a color developer for pressure-sensitive copying paper or heat-sensitive paper, as well as to a color developer containing a polyvalent-metal-modified product of the 3,5-di(α-methylbenzyl)salicylic acid derivative.

(2) Description of the Prior Art

Salicylic acid type compounds, when used as a color developer for pressure-sensitive paper or heat-sensitive paper, are generally excellent in clearness of developed color image, storage stability, etc. In the pressure-sensitive paper using a salicylic acid type compound as a color developer, however, there are problems of (a) slow color development due to the insufficient compatibility of said compound with a capsule oil used for dissolution of a color former and (b) insufficient water resistance of developed color image, i.e. disappearance of the said image by dissolution in water. Various attempts have been made in order to alleviate these problems. For example, it has been proposed to introduce an aromatic substituent into the salicylic acid skeleton The introduction of an aromatic substituent (e.g. a benzyl group) into, in particular, the 3- and 5-positions of the salicylic acid skeleton is effective. A color-developing sheet coated with a color developer consisting of, in particular, a polyvalent-metal-modified product of a salicylic acid compound with a benzyl group having a methyl group at the α-position, shows outstanding color developability and has excellent resistance to yellowing when exposed to sunlight, excellent stability of the developed color image and excellent resistance to yellowing by nitrogen oxides in air; therefore, the sheet is very advantageous in handling and storage. The above color developer, however, has drawbacks in that its slight solubility in water causes the disappearance of developed color image by water and its high melting point (190°-220° C.) makes slow the rate of its dissolution in a capsule oil containing a color precursor. This leads to inferior initial-stage color developability at low temperatures and limited use in cold districts.

(i) It is known to produce a 3,5-disubstituted salicylic acid from a corresponding substituted phenol and carbon dioxide according to the Kolbe-Schmitt reaction. For example, it is disclosed in Japanese Patent Publication No. 10856/1974 that 3,5-di(α,α-dimethylbenzyl)salicylic acid is produced from 2,4-di(α,α-dimethylbenzyl)phenol obtained from phenol and α-methylstyrene. This production process, however, generally incurs a high production cost because the reaction steps are many, the yield is low, and the reaction for introducing a carboxyl group is carried out under high temperature and high pressure conditions.

(ii) In order to overcome such a problem of high production cost, it was attempted to produce a similar salicylic acid compound by, for example, subjecting salicylic acid or a salicylic acid ester to alkylation.

It is known to react 1 mole of salicylic acid with 2 moles of 1-phenylethanol to obtain 5-[α-methyl-4-(α-methylbenzyl)-benzyl]salicylic acid or a mixture of 5-[α-methyl-4-(α-methylbenzyl)-benzyl]salicylic acid and 3,5-di(α-methylbenzyl)salicylic acid [Japanese Patent Application Kokai (Laid-Open) Nos. 100493/1986 and 96449/1987]. This production process has various problems The substituted salicylic acid obtained is a mixture of various compounds. Therefore, a monosubstituted salicylic acid or a mixture of a monosubstituted salicylic acid and a disubstituted salicylic acid is isolated in the form of a metal salt by a complicated procedure; when the metal salt of the mixture is used as a color developer for pressure-sensitive copying paper, the resulting color-developing paper has insufficient reproducibility in properties such as color developability, storage stability and the like.

(iii) It was proposed to react salicylic acid with a styrene compound in the presence of an aliphatic carboxylic acid using an organic sulfonic acid or an inorganic acid as a catalyst, to produce a disubstituted salicylic acid [Japanese Patent Application Kokai (Laid-Open) No. 91043/1990].

This production process is not advantageous industrially because the reaction is carried out at 90°-130° C. using an aliphatic carboxylic acid (e.g. acetic acid, propionic acid) and sulfuric acid or methanesulfonic acid in combination, with the acid used in an amount of 50% by weight or more based on the salicylic acid and accordingly the process has a problem of disposing a large amount of the waste acid. In this process, the reaction product is, for example, a mixture of 3,5-di(α-methylbenzyl)salicylic acid with 3-α-methylbenzyl-5-(1,3-diphenylbutyl)salicylic acid and 3-(1,3-diphenylbutyl)-5-α-methylbenzylsalicylic acid. When such a reaction product is used as a color developer for pressure-sensitive paper, the resulting color-developing paper has the same problems as in the above (ii).

(iv) With regard to the alkylation of an alkyl salicylate, it is known to react, for example, methyl salicylate with styrene in the presence of an alkanesulfonic acid to produce methyl 3,5-di(α-methylbenzyl)salicylate [Japanese Patent Publication No. 26772/1986]. In this production process using styrene, various styrene polymers and other by-products are formed. This process, similarly to the process for production of salicylic acid ester resin disclosed in Japanese Patent Application Kokai(-Laid-Open) No. 133780/1989 by the present inventors, is unable to suppress said reactions (resinification) even if the catalyst, the molar ratio of salicylic acid ester and styrene, the reaction temperature, etc. are varied.

In Comparative Example 1 (described later) which-was conducted for confirmation of the Example 1 of the above Japanese Patent Publication No. 26772/1986, the selectivity of methyl 3,5-di(α-methylbenzyl)salicylate was 43%. This is because not only a monosubstituted compound and a trisubstituted compound but also styrene polymers, a dimer adduct, etc. are formed. Moreover, the amount of alkanesulfonic acid used is large. Therefore, the above process is not advantageous.

SUMMARY OF THE INVENTION

The objects of the present invention are to develop an economical process for producing a 3,5-di(α-methylbenzyl)salicylic acid derivative which can be used as a color developer having excellent color developability and giving a developed color image with excellent resistance to yellowing by light, and to provide a color developer using said derivative and a color developer composition significantly improved in color developability at low temperatures and in water resistance of developed color image.

The above objects are achieved by a process comprising reacting a salicylic acid ester with an α-methylbenzyl halide in the presence of an acid catalyst to form a 3,5-di(α-methylbenzyl)salicylic acid ester and then hydrolyzing it to produce a 3,5-di(α-methylbenzyl)salicylic acid derivative.

In this case, when the reaction mixture is subjected, prior to being hydrolyzed, to vacuum distillation to isolate the 3,5-di(α-methylbenzyl)salicylic acid ester, the 3,5-di(α-methylbenzyl)salicylic acid derivative can be obtained at a purity of 99% or higher.

The present inventors also found that the above objects can further be achieved by reacting a salicylic acid ester with an α-methylbenzyl halide in the presence of an acid catalyst, then hydrolyzing the reaction product to produce an α-methylbenzyl-substituted salicylic acid derivative composition containing 60-90% by weight of a 3,5-di(α-methylbenzyl)salicylic acid derivative, converting the composition to a polyvalent-metal-modified product, and using the polyvalent-metal-modified product as a color developer.

The process of the present invention can produce a 3,5-di(α-methylbenzyl)salicylic acid derivative from inexpensive starting materials in a simple procedure and accordingly is preferable for industrial application.

Further, the color-developing sheet using a polyvalent-metal-modified product of an α-methylbenzyl-substituted salicylic acid derivative composition produced according to the present invention, composed mainly of a 3,5-di(α-methylbenzyl)salicylic acid derivative, has excellent color developability at low temperatures and accordingly is preferably used at low temperatures (conventional color-developing sheets of similar technique have had insufficient color developability at low temperatures). Also, the color-developing sheet is free from a problem of disappearance of developed color image by water. Therefore, the color-developing sheet can be used stably in the fields which have restricted the use of conventional color-developing sheets of similar technique.

DETAILED DESCRIPTION OF THE INVENTION

Figure 1:
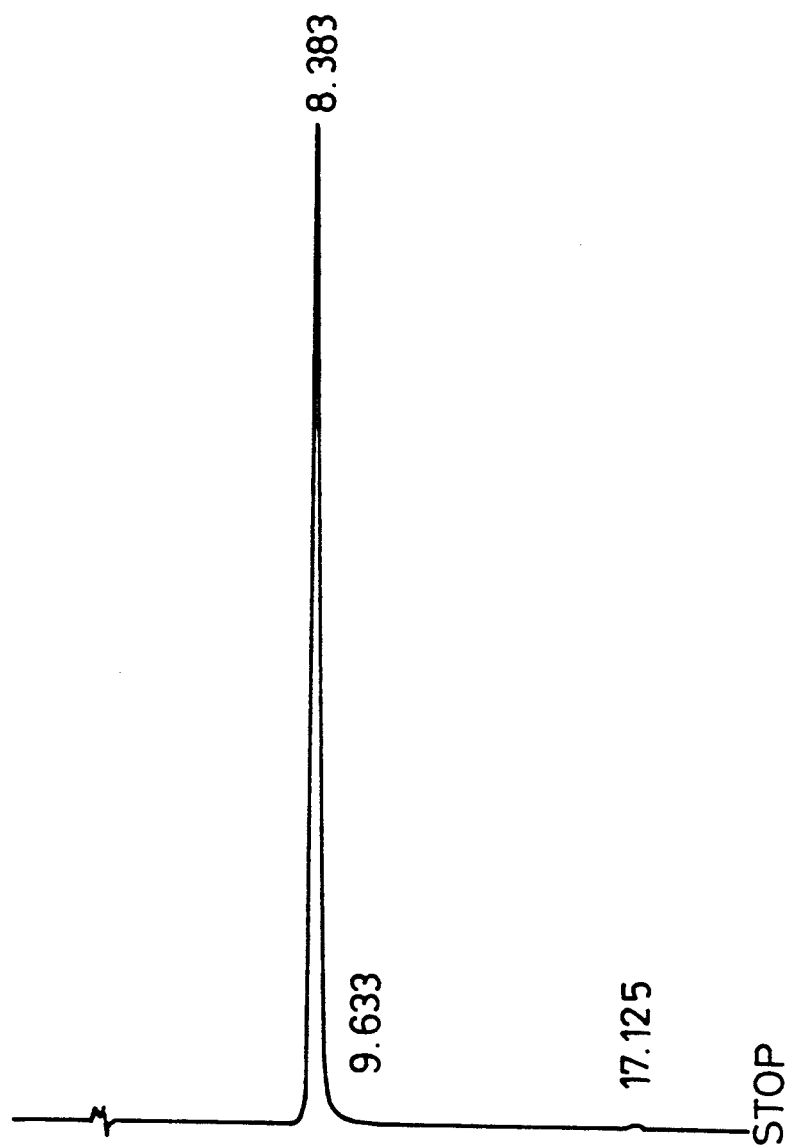
FIG. 1 shows an example of the analytical results when the 3,5-di(α-methylbenzyl)salicylic acid isolated according to the present process has been subjected to high-performance liquid chromatography.

The present invention provides (1) a process for producing a 3,5-di(α-methylbenzyl)salicylic acid derivative, which comprises reacting a salicylic acid ester represented by the general formula (I)

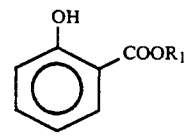

wherein $R_1$ represents an alkyl group, an aralkyl group or a cycloalkyl group each having at most 12 carbon atoms, with an α-methylbenzyl halide represented by the general formula (II)

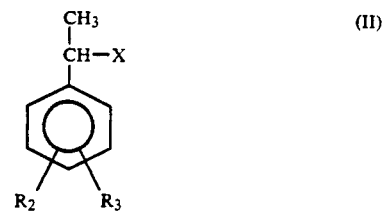

wherein $R_2$ and $R_3$ each represent a hydrogen atom or an alkyl group of 1-4 carbon atoms, and X represents a halogen atom, in the presence of an acid catalyst and hydrolyzing the resulting 3,5-di(α-methylbenzyl)salicylic acid ester, (2) a polyvalent-metal-modified product of the α-methylbenzyl-substituted salicylic ( acid derivative composition containing 60-90% by weight of a 3,5-di(α-methylbenzyl)salicylic acid derivative, obtained by the above process, and (3) a color-developing sheet using the polyvalent-metal-modified product as a color developer.

The salicylic acid ester used in the present invention includes methyl salicylate, ethyl salicylate, n-propyl salicylate, isopropyl salicylate, isoamyl salicylate, tert-octyl salicylate, nonyl salicylate, dodecyl salicylate, cyclohexyl salicylate, benzyl salicylate, α-methylbenzyl salicylate, etc. However, the salicylic acid ester is not restricted to these compounds. Methyl salicylate and ethyl salicylate are preferable industrially.

In the α-methylbenzyl halide used in the present invention, the halogen includes chlorine and bromine. Chlorine is preferable. Accordingly, the α-methylbenzyl halide includes α-methylbenzyl chloride, o-methyl-α-methylbenzyl chloride, p-methyl-α-methylbenzyl chloride, m-methyl-α-methylbenzyl chloride, o-ethyl-α-methylbenzyl chloride, p-ethyl-α- methylbenzyl chloride, p-isopropyl-α-methylbenzyl chloride, 2,3-dimethyl-α-methylbenzyl chloride, 2,4-dimethyl-α-methlbenzyl chloride, 2,5-dimethyl-α-methylbenzyl chloride and 3,4-dimethyl-α-methylbenzyl chloride. However, the α-methylbenzyl halide is not restricted to these compounds. Of these compounds, α-methylbenzyl chloride and p-methyl-α-methylbenzyl chloride are preferable.

The amount of the α-methylbenzyl halide used in the process of the present invention is preferably 1.5-3 moles per mole of the salicylic acid ester represented by the general formula (I). When the amount is less than 1.5 moles or more than 3 moles, the yield of a 3,5-di(α-methylbenzyl)salicylic acid ester as a main precursor is low.

As the acid catalyst used in the present process, there can be mentioned Lewis acids such as ferric chloride, zinc chloride, aluminum chloride, stannic chloride, titanium tetrachloride and boron trifluoride, and superacids such as perfluoroalkanesulfonic acid (e.g. trifluoromethanesulfonic acid) and perfluoroalkanesulfonic acid resin [e.g. Nafion H (trademark of Du Pont)]. Of these, zinc chloride is particularly preferable.

The amount of the catalyst used is 0.05-200 mole % and, in view of the economy, preferably 0.1-100 mole % based on the salicylic acid ester.

The reaction temperature is 0°-180° C., preferably 5°-80° C., more preferably 10°-40° C. The reaction time is ordinarily 1-120 hours.

In the reaction of the salicylic acid ester with the α-methylbenzyl halide, a solvent may be used as necessary. As the solvent, there can be used those inactive to the reaction, for example, halogenated hydrocarbons such as 1,2-dichloroethane and 1,1,2-trichloroethane, and organic acids such as acetic acid and propionic acid. The amount of the solvent when used is desirably not more than 30 (volume/weight) times the total amount of the raw materials in view of the economy.

In the present invention, the reaction of the salicylic acid ester with the α-methylbenzyl halide is generally carried out by feeding necessary amounts of the salicylic acid ester of the general formula (I), the α-methylbenzyl halide of the general formula (II) and the catalyst at one time and reacting them at a predetermined temperature, or by feeding the salicylic acid ester and the catalyst first and then adding the α-methylbenzyl halide dropwise to react them.

The end point of the reaction can be determined by examining the decrease of the raw materials, i.e. the salicylic acid ester and the α-methylbenzyl halide by means of high-performance liquid chromatography.

The hydrolysis is carried out according to an ordinary method using an aqueous acid or alkali solution. The hydrolysis using an aqueous acid solution is carried out using water and an acid, i.e. a mineral acid (e.g. hydrochloric acid, sulfuric acid), a combination of sulfuric acid and acetic acid, an organic sulfonic acid (e.g. benzenesulfonic acid, p-toluenesulfonic acid, chlorobenzenesulfonic acid, methanesulfonic acid), a Lewis acid (e.g. aluminum chloride, zinc chloride, stannic chloride), or a superacid (e.g. trifluoromethanesulfonic acid, Nafion H).

The hydrolysis using an aqueous alkali solution is generally carried out using water and sodium hydroxide or potassium hydroxide.

The ratio of the acid or alkali and water can be selected freely but is generally 1:100 to 99:1, preferably 5:95 to 95:5 by weight.

The amount of the acid or alkali used in the hydrolysis can be any amount relative to the amount of the salicylic acid ester as a raw material. However, the amount of the acid is generally 0.05-30 moles per mole of the salicylic acid ester depending upon the intensity of the acid, and the amount of the alkali is an equivalent to 30 moles.

The reaction temperature is 50°-200° C., preferably 80°-160° C. The reaction time is 1-50 hours.

In order to shorten the reaction time, it is possible to add, as a reaction accelerator, a phase-transfer catalyst such as quaternary phosphonium salt, crown ether, cryptate or polyethylene glycol.

The hydrolysis reaction is carried out ordinarily using no organic solvent, but may use an organic solvent. As such an organic solvent, there may be used aprotic polar solvents such as N-methylformamide, N,N-dimethylformamide, N,N-dimethylacetamide, dimethyl sulfoxide, sulfolane, 1,3-dimethyl-2-imidazolidinone, N-methylpyrrolidone and hexamethylphosphoric triamide, and glycols such as ethylene glycol, polyethylene glycol dialkyl ether, 2-methoxyethanol and 2-ethoxyethanol. There may further be used solvents having no miscibility with water, such as toluene, xylene, monochlorobenzene, 1,2-dichloroethane and 1,1,2-trichloroethane. The amount of the solvent used is sufficiently 0.5-10 (volume/weight) times the total amount of the raw materials.

The reaction mixture after the hydrolysis contains a reaction product composed of 60-90% by weight of a 3,5-di(α-methylbenzyl)salicylic acid derivative, 0-40% by weight of a 3-or 5-(α-methylbenzyl)salicylic acid derivative (hereinafter abbreviated to a monosubstituted salicylic acid derivative) and 0-40% by weight of a salicylic acid compound formed by the reaction of said 3,5-di(α-methylbenzyl)salicylic acid derivative with an α-methylbenzyl group (said salicylic acid compound is hereinafter abbreviated to a trisubstituted salicylic acid derivative), in which reaction product said three components occupy 95% by weight or more of the total and the remainder is occupied by aromatic salicylic acid resins and oligomers of α-methylbenzyl halide Since the hydrolysis is carried out substantially quantitatively, the proportions of the corresponding components of the ester form before the hydrolysis are thought to be about the same as above.

The above reaction product which is composed mainly of a 3,5-di(α-methylbenzyl)salicylic acid derivative and which may further contain mono- and/or trisubstituted salicylic acid derivative, is referred, in the present invention, to an α-methylbenzyl-substituted salicylic acid derivative composition.

In order to obtain a 3,5-di(α-methylbenzyl)salicylic acid derivative of high purity (99% or higher), the reaction product before hydrolysis is subjected to vacuum distillation to separate a 3,5-di(α-methylbenzyl)salicylic acid ester and the ester is hydrolyzed.

This production process is inexpensive as compared with the conventionally known process using phenol as a raw material and has a high selectivity as compared with the process using a salicylic acid ester and a styrene compound; therefore, it is a very advantageous process in industrial application.

In this process, if the salicylic acid ester as a raw material is replaced by salicylic acid, the reactivity is low owing to the presence of an electron-attractive carboxyl group and a reaction temperature higher than in the present invention is required. Under such conditions, the selectivity of a disubstituted salicylic acid derivative is as low as 40-50%.

In order to obtain a reaction product from the reaction mixture after hydrolysis, the reaction mixture is neutralized and, when the precipitation of crystals is over, the crystals are isolated to obtain the reaction product. When the reaction product is dissolved in the solvent used, the solvent is removed by distillation or the reaction mixture is added to water, to obtain the reaction product as crystals.

In some cases, it is possible to carry out recrystallization using an appropriate solvent to obtain crystals. The degree of progress of reaction or the purity of isolated product can be determined by high-performance liquid chromatography.

The following is a description of the production of a polyvalent-metal-modified product of the 3,5-di(α-methylbenzyl)salicylic acid derivative or the α-methylbenzyl-substituted salicylic acid derivative composition (hereinafter the salicylic acid derivative and the salicylic acid derivative composition are generically referred to simply as salicylic acid compound).

The polyvalent-metal-modified product is produced by reacting an alkali metal salt of the salicylic acid compound with a water-soluble polyvalent metal salt in water or in a solvent in which the two metal salts are soluble.

The salicylic acid compound is dispersed in an aqueous solution, an alcohol solution or an aqueous alcohol solution each containing a hydroxide, carbonate or alkoxide of an alkali metal in an amount at least equivalent to the carboxyl group of the salicylic acid compound, and is dissolved therein at 0°–100° C.; to the resulting solution is added a water-soluble polyvalent metal salt as is or in the form of an aqueous solution, an alcohol solution or an aqueous alcohol solution; a reaction is carried out at 0°–100° C. to obtain a polyvalent metal salt of the salicylic acid compound as a precipitate. It.-is desirable to react the water soluble polyvalent metal salt of about 0.5–1 equivalent to the carboxyl group of the salicylic acid compound.

The metal of the polyvalent-metal-modified product used in the present invention includes metals excluding alkali metals such as lithium, sodium and potassium. As preferable polyvalent metals, there can be mentioned calcium, magnesium, aluminum, copper, zinc, tin, barium, cobalt and nickel. Of these, zinc is particularly useful.

The thus obtained polyvalent-metal-modified product of the salicylic acid compound exhibits excellent properties when used as a color developer. In using the polyvalent-metal-modified product as a color developer, it is ground by a grinder, for example, a sand grinding mill so as to have an appropriate particle size. In actual use, the ground polyvalent-metal-modified product is suspended or dissolved in a solvent to convert into a desired form. It is possible to use the polyvalent-metal-modified product in combination with a known color developer such as inorganic solid acid (e.g. activated clay), organic polymer (e.g. phenol-formaldehyde resin) or other aromatic carboxylic acid metal salt. It is also possible to use the polyvalent-metal-modified product in combination with at least one oxide, hydroxide or carbonate of polyvalent metals selected from the group consisting of zinc, magnesium, aluminum, lead, titanium, calcium, cobalt, nickel, manganese and barium.

The preparation of a color-developing sheet used for pressure-sensitive copying from the color developer of the present invention can be carried out, for example, by (1) a method wherein an aqueous coating is prepared using an aqueous suspension of the polyvalent-metal-modified product and it is coated on a substrate such as paper or the like, (2) a method wherein a paper is manufactured in the presence of the polyvalent-metal-modified product, and (3) a method wherein a coating is prepared using a solution or suspension of the polyvalent-metal-modified product in an organic solvent and it is coated on a substrate.

In order to form, by coating, a color developer layer on a substrate such as paper or the like, it is desirable that the color developer have an appropriate viscosity and appropriate coatability. Therefore, the above aqueous suspension or the above solution or suspension in solvent is mixed with kaolin, clay, calcium carbonate, starch and synthetic or natural latex to prepare a coating of appropriate viscosity and coatability. In the coating, the proportion of the color developer component is desirably 10–70% based on the total solid content. When the proportion is less than 10%, insufficient color development is obtained. When the proportion is more than 70%, the resulting color-developing sheet has degraded surface properties. The amount of the coating applied is at least 0.5 g/m², preferably 1–10 g/m² in terms of dry weight.

The present invention is hereinafter described in detail with reference to Examples.

Using each of the products obtained in Examples and Comparative Examples as a color developer, color-developing sheets for pressure-sensitive copying were prepared as follows and these sheets were measured for properties according to the following methods: The results of the property measurements are shown in Table 1 and Table 2.

1. Preparation of color-developing sheet

Using each of the metal-modified products of salicylic acid compounds, obtained in Examples 2, 5, 6, 7 and 8 (described later), as a color developer, their suspensions having the following formulation were prepared by means of a sand grinding mill.

| Color developer | 6 parts by weight |
|---|---|
| Aqueous solution containing polyvinyl alcohol (Kurare #117) | 3 parts by weight |
| Water | 22.5 parts by weight |

Using each of the suspensions, coatings having the following formulation were prepared.

| Suspension | 10 parts by weight |
|---|---|
| Light calcium carbonate | 10 parts by weight |
| Starch | 0.8 part by weight |
| Synthetic rubber latex | 0.8 part by weight |
| Water | 32.5 parts by weight |

Each of the coatings was coated on a high-quality paper so that the coated amount as dried became 5.0–5.5 g/m², and dried to obtain color-developing sheets.

2. Color-developing speed and developed color density
(conducted in air-conditioned rooms of 5° C. and 60% R.H. and 20° C. and 65% R.H.)

A sample color-developing sheet coated with an aqueous coating was contacted with a blue-color-developing sheet on the market [NW-40T (trade name), a product of Jujo Paper Co., Ltd.]containing Crystal Violet Lactone (CVL) as a main pressure-sensitive color precursor, in such a way that the coated sides of the two sheets faced each other. They were typed by an electronic typewriter to develop a color.

The developed color was measured for density one minute and 30 seconds after the typing and 24 hours after the typing, and the densities were each expressed as Y value.

3. Light fastness of developed color image

A sample color-developing sheet, which had been subjected to color development in the manner described in the above 2, was exposed to light for 2 hours (and for 4 hours) in a carbon arc fade meter (manufactured by Suga Testing Machine Co., Ltd.). After the exposure, the reflectance of the developed color image was measured by Σ-80 Color Difference Meter, and expressed as Y value.

The smaller the Y value and the smaller its difference from the Y value before the test, the less the fading of the developed color image by light and the more preferable the color image.

4. Plasticizer resistance

A dioctyl phthalate (DOP) microcapsule coated paper sheet was prepared by forming microcapsules, which contained DOP as a core substance, had an average size of 5.0 μm, and were equipped with melamine-formaldehyde resin capsule walls, adding thereto a small amount of a starch-type liquid binder to obtain a coating solution, applying the coating solution onto a high-quality paper by an air-knife coater so that the coated amount as dried became 5 g/m$^2$, and then drying the thus-coated paper. The DOP microcapsule coated paper sheet was contacted with the color-developing sheet with a developed color image produced in the above 2, in such a way that the coated sides of the two sheets faced each other. They were allowed to pass through a super calender roll having a linear pressure of 100 kg/cm, whereby DOP was allowed to penetrate uniformly into the colored surface of the color-developing sheet.

One hour after the passing, the reflectance of the color-developing sheet was measured by Σ-80 Color Difference meter and expressed as Y value. The smaller the Y value and the smaller its difference from the Y value before the test, the better the plasticizer resistance of the developed color image.

5. Water resistance of developed color image

A sample color-developing sheet, which had been subjected to color development in the same manner as in the above 2, was dipped in water for 2 hours. Change in density of the developed color image was observed visually 6. Yellowing property of color-developing sheet 6-1 Yellowing by NO$_x$ Following JIS L-1055 (Testing Method for NO$_x$ Gas Fastness of Dyed Materials and Dyes), a sample color-developing sheet was stored for 1 hour in a closed vessel of an atmosphere of NO$_x$ gas generated by the reaction of NaNO$_2$ (sodium sulfite) and H$_3$PO$_4$ (phosphoric acid), to examine the degree of its yellowing.

One hour after completion of the storage, the reflectance of the color-developing sheet was measured by Σ-80 Color Difference Meter, and expressed as WB value. The greater the WB value and the smaller its difference from the WB value of a sheet not exposed to NO$_x$ gas (expressed as untested sheet in Table 2), the smaller the yellowing property in an NO$_x$ atmosphere.

6-2 Yellowing by light

A sample color-developing sheet was exposed to light for 4 hours in a carbon arc fade meter (manufactured by Suga Testing Machine Co., Ltd.). After the exposure, the reflectance of the sample color-developing sheet was measured by Σ-80 Color Difference Meter and expressed as WB value. The greater the WB value and the smaller its difference from the WB value of an unexposed sheet (expressed as untested sheet in Table 2), the smaller the yellowing property upon exposure to light.

EXAMPLE 1

Into a flask were fed 152.2 g (1 mole) of methyl salicylate, 281.2 g (2 moles) of 1-chloroethylbenzene and 3 g of trifluoromethanesulfonic acid. They were subjected to reaction at room temperature (20° C.) for 5 days.

After completion of the reaction, 1,500 ml of toluene was fed to dissolve the reaction mixture. Then, 100 ml of water was added. Stirring was carried out at 60°–70° C. for 0.5 hour and then the mixture was allowed to stand until it separated into two layers, i.e. an organic layer and an aqueous layer (a lower layer). The lower aqueous layer was removed, and the organic layer was subjected to distillation to remove the solvent. The residue was subjected to high-performance liquid chromatography (HLC) and found to consist of 3% of methyl ester of monosubstituted salicylic acid, 89.5% of methyl ester of disubstituted salicylic acid and 7.5% of methyl ester of trisubstituted salicylic acid. The residue was then subjected to vacuum distillation at 1–3 mmHg to take out a distillate fraction of 213°–218° C. to obtain 291 g (yield: 81%) of methyl ester of 3,5-di(α-methylbenzyl)salicylic acid.

90 g (0.25 mole) of the thus obtained methyl ester of 3,5-di(α-methylbenzyl)salicylic acid and 28.9 g of a 40% aqueous sodium hydroxide solution (containing 0.275 mole of NaOH) were fed into a 500-ml flask and reacted at 95°–105° C. for 3 hours to complete hydrolysis. Then, 430 ml of water was added to dissolve the reaction mixture. The solution was neutralized with sulfuric acid and filtered. The filtrate was water-washed and dried to obtain 84.7 g (yield: 98%) of 3,5-di(α-methylbenzyl)salicylic acid having a purity of 99% or higher.

|  | C | H | O |  |
|---|---|---|---|---|
| Calculated | 79.77 | 6.36 | 13.87 | (C$_{24}$H$_{24}$O$_3$) |
| Observed | 80.16 | 6.31 | — |  |

H-NMR (CDCl$_3$):
1.6 (m,6H), 4.1 (m,1H), 4.6 (m,1H), 7.1–7.3 (m,1H), 7.65 (m,1H), 9.4 (Br,1H), 10.5 (s,1H).
MS: m/z=346 (M+).

The results of measurement by HLC made under the following conditions are shown in FIG. 1.

Chromatograph: LIQUID CHROMATOGRAPH LC-3A (a product of Shimadzu).
Column: YMC-Pack AM-312.
Mobile phase: Acetonitrile/MeOH/water/trifluoroacetic acid=725 ml/100 ml/175 ml/0.5 g
Flow rate: 1 ml/min.
Detector: SPD-2A (UV-254 nm).
Wave analysis: Shimadzu Chromatopack C-R3A.

EXAMPLE 2

69.2 g (0.2 mole) of the 3,5-di(α-methylbenzyl)salicylic acid obtained in Example 1 was dissolved in an aqueous alkali solution obtained by dissolving 8.8 g of 95% sodium hydroxide (0.21 mole as NaOH) in 500 g of water. The resulting aqueous solution was dropwise added, in 1 hour, to an aqueous solution obtained by dissolving 31.6 g of zinc sulfate heptahydrate in 300 ml of water, and the mixture was aged for 1 hour. Then, the mixture was filtered. The filtrate was water-washed and dried to obtain 70 g of zinc salt of 3,5-di(α-methylbenzyl)salicylic acid.

EXAMPLE 3

Into a flask were fed 190.3 g (1.25 moles) of methyl salicylate and an acid catalyst obtained by disolving 5 g of zinc chloride in 2 g of concentrated hydrochloric acid. The flask inside temperature was elevated to 35° C., and 404.3 g (2.87 moles) of 1-chloroethylbenzene was dropwise added in 2 hours while the same temperature was maintained. After completion of the dropwise addition, the mixture was aged at the same temperature for 20 hours. Then, 750 ml of toluene was added to dissolve the mixture, after which 150 ml of water was added. Stirring was carried out at 60°-70° C. for 0.5 hour, and then the mixture was allowed to stand until it separated into two layers, i.e. an organic layer and an aqueous layer (a lower layer). The lower aqueous layer was removed and the organic layer was subjected to distillation to remove the solvent. The residue was found by HLC to consist of 2.9% of methyl ester of monosubstituted salicylic acid, 80% of methyl ester of disubstituted salicylic acid and 11.2% of methyl ester of trisubstituted salicylic acid. The residue was subjected to vacuum distillation at 1-3 mmHg to take out a distillate fraction of 213°-218° C. to obtain 338 g (yield: 75%) of methyl ester of 3,5-di(α-methylbenzyl)salicylic acid. This product was hydrolyzed with a 40% aqueous sodium hydroxide solution in the same manner as in Example 1 to obtain 318 g (yield: 98%) of 3,5-di(α-methylbenzyl)salicylic acid of 99% purity.

EXAMPLE 4

Into a flask were fed 16.6 g (0.1 mole) of ethyl salicylate, 33.8 g (0.24 mole) of 1-chloroethylbenzene and 0.3 g of trifluoromethanesulfonic acid. They were subjected to reaction at 20° C. for 30 hours. After completion of the reaction, 150 ml of toluene was added to dissolve the reaction mixutre. Then, 50 ml of water was added, and stirring was carried out at 60°-70° C. for 0.5 hour. The mixture was allowed to stand until it separated into two layers, i.e. an organic layer and an aqueous layer (a lower layer). The lower aqueous layer was removed, and in the same manner as in Example 1, the organic layer was subjected to distillation to remove the solvent. The residue was found by HLC to consist of 6% of ethyl salicylate, 4.5% of ethyl ester of monosubstituted salicylic acid, 76.8% of ethyl ester of disubstituted salicylic acid and 12.7% of ethyl ester of trisubstituted salicylic acid. The residue was subjected to vacuuum distillation to obtain 26.2 g (yield: 70%) of ethyl ester of 3,5-di(α-methylbenzyl)salicylic acid. The ester was hydrolyzed with 40% sodium hydroxide to obtain 23.7 g (yield: 98%) of 3,5-di(α-methylbenzyl)salicylic acid of 99% purity.

EXAMPLE 5

Into a flask were fed 76.1 g (0.5 mole) of methyl salicylate, 1.5 g of stannic chloride (SnCl$_2$) and 154.6 g (1.1 moles) of 1-chloroethylbenzene. They were subjected to reaction at 20°-25° C. for 5 hours. Then, the reaction mixture was heated to 70° C., and 200 ml of water was added. The resulting mixture was heated to 95°-98° C. and 170 g of 15% sodium hydroxide was dropwise added in 2 hours. The mixture was aged at 98°-100° C. for 5 hours to complete hydrolysis The hydrolyzate was found by HLC to consist of 2% of salicylic acid, 13% of monosubstituted salicylic acid, 67% of disubstituted salicylic acid, 17% of trisubstituted salicylic acid and 1% of others. 700 ml of water was added for dilution The dilution product was adjusted to pH 9 with sulfuric acid. Thereto was dropwise added 180 g of a 43% aqueous zinc sulfate solution, at 30° C. in 1 hour. The mixture was aged for 1 hour and filtered. The filtrate was water-washed and dried to obtain 200 g of zinc salt of an α-methylbenzyl-substituted salicylic acid composition.

EXAMPLE 6

Into a flask were fed 76.1 g (0.5 mole) of methyl salicylate, 1 g of antimony chloride (SbCl$_5$) and 147.6 g (1.05 moles) of 1-chloroethylbenzene. They were subjected to reaction at 30°-35° C. for 8 hours. The reaction mixture was heated to 70° C., and 200 ml of hot water was added. The resulting mixture was heated to 95°-98° C. Thereto was dropwise added 170 g of a 15% queous sodium hydroxide solution in 2 hours. The mixture was aged at 98°-100° C. for 5 hours to complete hydrolysis. The hydrolyzate was found by HLC to consist of 12% of monosubstituted salicylic acid, 68% of disubstituted salicylic acid, 18% of trisubstituted salicylic acid and 2% of others. 700 ml of water was added for dilution. The dilution product was adjusted to pH 9 with sulfuric acid. Thereto was dropwise added 180 g of a 43% aqueous zinc sulfate solution at 30° C. in 1 hour. The mixture was aged for 1 hour and filtered. The filtrate was water-washed and dried to obtain 200 g of zinc salt of an α-methylbenzyl-substituted salicylic acid composition.

EXAMPLE 7

Into a flask were fed 76.1 g (0.5 mole) of methyl salicylate and an acid obtained by dissolving 2 g of zinc chloride in 0.8 g of concentrated hydrochloric acid. The flask inside temperature was elevated to 35° C. Thereto was dropwise added 161.7 g (1.15 moles) of 1-chloroethylbenzene at the same temperature in 2 hours. After completion of the dropwise addition, the mixture was subjected to reaction at the same temperature for 20 hours. The reaction mixture was heated to 70° C., and 200 ml of hot water was added. The mixture was heated to 95°-98° C. and 170 g of a 15% aqueous sodium hydroxide solution was dropwise added in 2 hours. The mixture was aged at 98°-100° C. for 5 hours to complete hydrolysis. The hydrolyzate was found by HLC to consist of 7% of monosubstituted salicylic acid, 80% of disubstituted salicylic acid and 13% of trisubstituted salicylic acid. 700 ml of water was added for dilution. The dilution product was adjusted to pH 9 with sulfuric acid. Thereto was dropwise added 180 g of a 43% aqueous zinc sulfate solution at 30° C. in 1 hour. The mixture was aged for 1 hour and filtered. The filtrate was water-washed and dried to obtain 200 g of zinc salt of an α-methylbenzyl-substituted salicylic acid composition.

EXAMPLE 8

Figure 2:
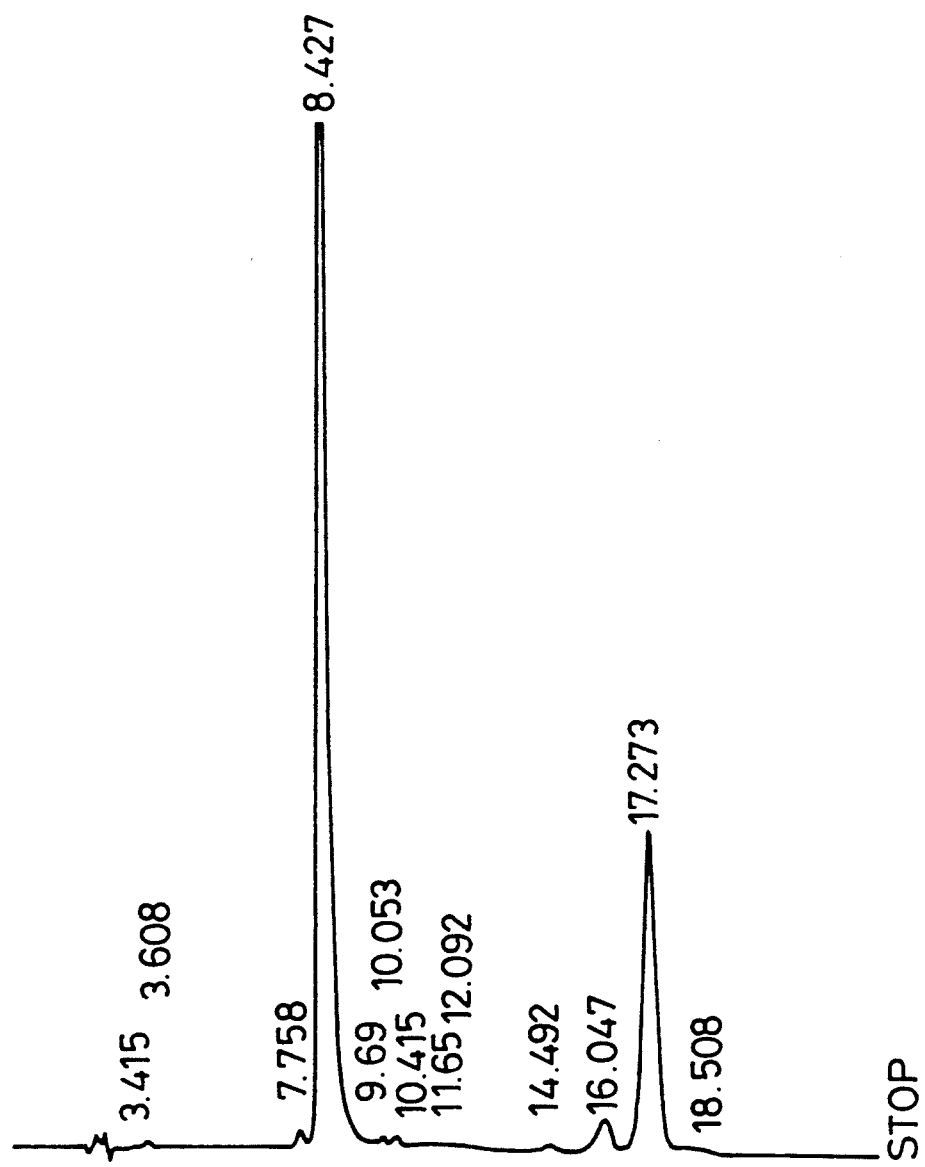
FIG. 2 shows an example of the analytical results when the α-methylbenzyl-substituted salicylic acid derivative composition obtained according to the present process has been subjected to high-performance liquid chromatography.

Into a flask were fed 76.1 g (0.5 mole) of methyl salicylate, 1.5 g of trifluoromethanesulfonic acid and 154.6 g (1.1 moles) of 1-chloroethylbenzene. They were subjected to reaction at 20°-25° C. for 5 days. The reaction mixture was heated to 70° C. and 200 ml of hot water was added. The mixture was heated to 95°-98° C. Thereto was dropwise added 170 g of a 15% aqueous sodium hydroxide solution in 2 hours. The mixture was aged at 98°-100° C. for 5 hours to complete hydrolysis. The hydrolyzate was found by HLC to consist of 88% of disubstituted salicylic acid, 11% of trisubstituted salicylic acid and 1% of others (FIG. 2). In FIG. 2, RT 8.427 indicates 3,5-di(α-methylbenzyl)salicylic acid. 700 ml of water was added for dilution. The dilution product was adjusted to pH 9 with sulfuric acid. Thereto was dropwise added 180 g of a 43% aqueous zinc sulfate solution at 30° C. in 1 hour The mixture was aged for 1 hour and filtered. The filtrate was water-washed and dried to obtain 200 g of zinc salt of 3,5-di(α-methylben-zyl)salicylic acid.

COMPARATIVE EXAMPLE 1

Figure 3:
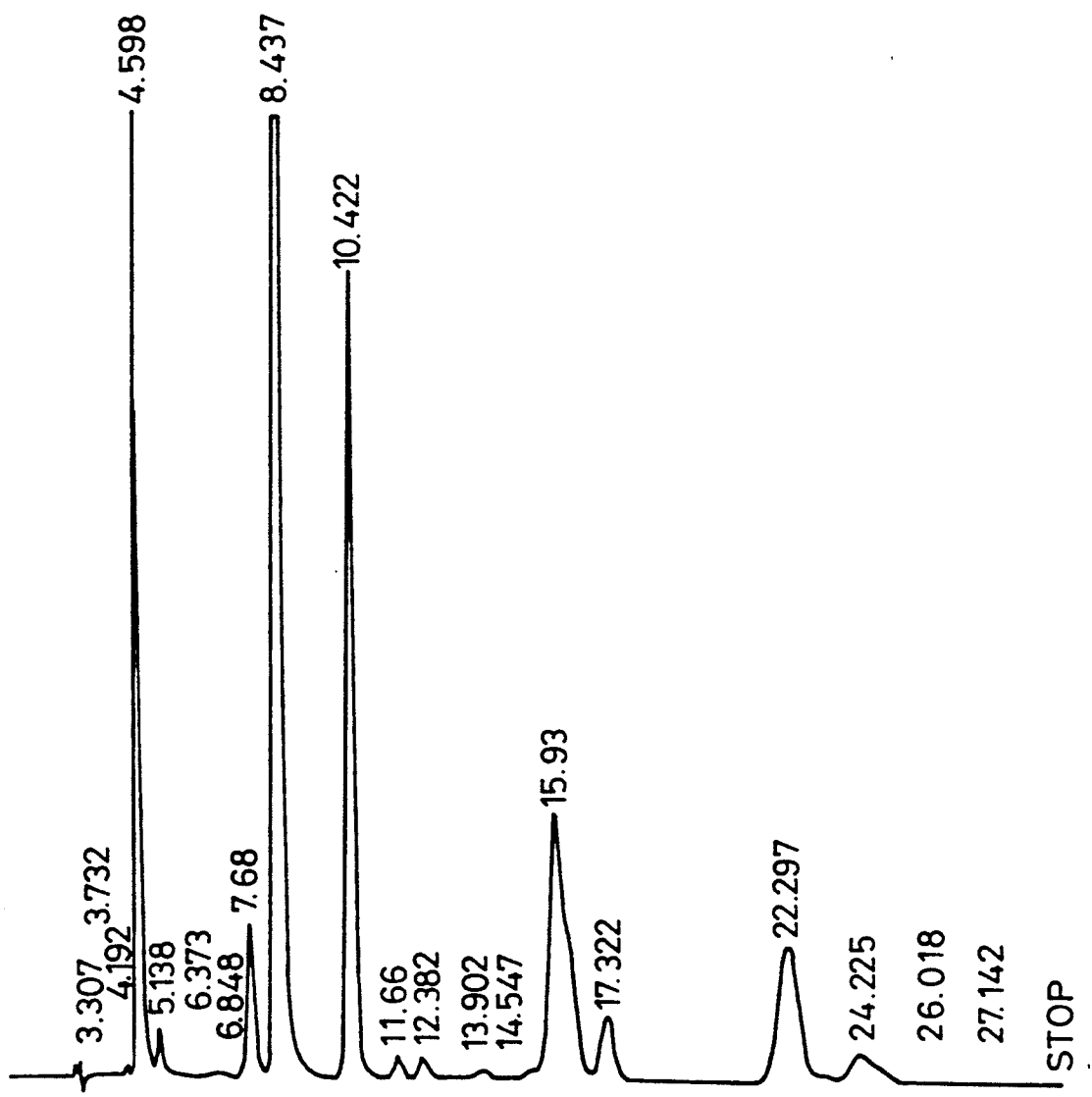
FIG. 3 shows an example of the analytical results when the 3,5-di(α-methylbenzyl)salicylic acid-containing oily substance obtained according to a conventional process has been subjected to high-performance liquid chromatography.

Into a flask were fed 76.1 g (0.5 mole) of methyl salicylate and 10 g of methanesulfonic acid. While the flask inside temperature was maintained at 60°-65° C., 140 g (1.346 moles) of styrene was dropwise added in 14 hours. After completion of the dropwise addition, the mixture was aged at the same temperature for 30 minutes. The reaction mixture was subjected to hydrolysis with a 40% aqueous sodium hydroxide solution in the same manner as in Example 1. Then, neutralization with sulfuric acid was carried out to obtain an oily product containing 3,5-di(α-methylbenzyl)salicylic acid The oily product was found by HLC to contain 43.3% of 3,5-di(α-methylbenzyl)salicylic acid. The results of HLC are shown in FIG. 3 In FIG. 3, RT 8.437 indicates 3,5-di(α-methylbenzyl)salicylic acid.

It was tried to convert the oily product to a zinc derivative as in Example 8. However, a gummy or block-like substance was formed, making difficult filtration, water washing and drying.

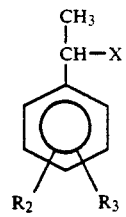

wherein $R_2$ and $R_3$ each represent a hydrogen atom or an alkyl group of 1-4 carbon atoms, and X represents a halogen atom, in the presence of an acid catalyst and hydrolyzing the resulting 3,5-di(α-methylbenzyl)salicylic acid ester.

2. A process according to claim 1, wherein the 3,5-di(α-methylbenzyl)salicylic acid ester is separated from the reaction mixture by vacuum distillation, prior to the hydrolysis thereof.

3. A process according to claim 1, wherein $R_1$ is methyl.

4. A process according to claim 1, wherein $R_2$ and $R_3$ are hydrogen atoms and X is a chlorine atom.

TABLE 1

Color Developability and Developed Color Properties of Color-Developing Sheets

| | Blue color development (20° C., 65% R.H.) | | | | | Low-temp. color development (5° C., 60% R.H.) | |
|---|---|---|---|---|---|---|---|
| | Developed color density of color-developing sheet (Y) | | Light fastness of developed color image (Y) | | Plasticizer resistance of developed color image (Y) | Water resistance of developed color image | Developed color density of color-developing sheet (Y) | |
| Example | 1.5 minutes later | 24 hours later | 2 hours | 4 hours | | | 1.5 minutes later | 24 hours later |
| 2 | 59.9 | 56.1 | 65.0 | 74.1 | 60.6 | Disappeared | 69.9 | 58.5 |
| 5 | 56.9 | 54.9 | 64.5 | 74.0 | 57.9 | Good | 62.3 | 56.9 |
| 6 | 56.9 | 54.5 | 64.5 | 74.0 | 57.8 | Good | 62.5 | 56.5 |
| 7 | 57.2 | 55.9 | 64.8 | 73.8 | 58.4 | Good | 63.0 | 57.9 |
| 8 | 58.4 | 55.9 | 64.9 | 74.1 | 59.0 | Nearly good | 65.2 | 57.9 |

TABLE 2

Yellowing of Color-Developing Sheets

| | | Tested sheet | |
|---|---|---|---|
| Example | Untested sheet (WB value) | Yellowing by NOx (WB value) | Yellowing by light (WB value) |
| 2 | 84.5 | 81.4 (3.1) | 77.1 (7.4) |
| 5 | 84.5 | 81.2 (3.3) | 76.8 (7.7) |
| 6 | 84.5 | 81.2 (3.3) | 76.8 (7.7) |
| 7 | 84.3 | 81.6 (2.7) | 76.8 (7.5) |
| 8 | 84.3 | 81.5 (2.8) | 76.9 (7.4) |

Each figure in parentheses indicates a difference of the WB value of untested sheet and the WB value of tested sheet.

What is claimed is:

1. A process for producing a 3,5-di(α-methylbenzyl)-salicylic acid derivative, which comprises reacting a salicylic acid ester represented by the general formula (I)

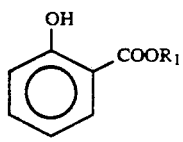

wherein $R_1$ represents an alkyl group, an aralkyl group or a cycloalkyl group each having at most 12 carbon atoms, with an α-methyl-benzyl halide represented by the general formula (II)

5. A process according to claim 1, wherein $R_1$ is methyl; wherein $R_2$ and $R_3$ are hydrogen atoms and X is a chlorine atom; and wherein the thus-produced 3,5-di(α-methylbenzyl)salicylic acid ester is separated from the reaction mixture by vacuum distillation prior to the hydrolysis thereof.

6. An α-methylbenzyl-substituted salicylic acid derivative composition comprising 60-90% by weight of a 3,5-di(α-methylbenzyl)salicylic acid derivative and produced by reacting a salicylic acid ester represented by the general formula (I)

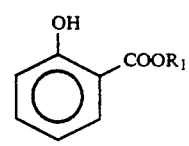

wherein $R_1$ respresents an alkyl group, an aralkyl group or a cycloalkyl group each having at most 12 carbon atoms, with an α-methyl-benzyl halide represented by the general formula (II)

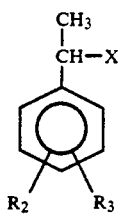

(II)

wherein $R_2$ and $R_3$ each represent a hydrogen atom or an alkyl group of 1–4 carbon atoms, and X represents a halogen atom, in the presence of an acid catalyst and hydrolyzing and resulting 3,5-di(α-methylbenzyl)salicylic acid ester.

7. An α-methylbenzyl-substituted salicylic acid derivative composition according to claim 6, which comprises 0–40% by weight of an α-methylbenzyl-monosubstituted salicylic acid derivative and 0–40% by weight of an α-methylbenzyl-trisubstituted salicylic acid derivative and which with the 60–90% by weight of the 3,5-di(α-methylbenzyl)salicylic acid derivative and constitute 95% by weight or more of the composition.

8. An α-methylbenzyl-substituted salicylic acid derivative composition according to claim 6, wherein $R_1$ is methyl.

9. An α-methylbenzyl-substituted salicylic acid derivative composition according to claim 6, wherein $R_2$ and $R_3$ are hydrogen atoms and X is a chlorine atom.

10. An α-methylbenzyl-substituted salicylic acid derivative composition according to claim 6, wherein $R_1$ is methyl; and wherein $R_2$ and $R_3$ are hydrogen atoms and X is a chlorine atom.

11. A polyvalent-metal-modified reaction product of an α-methylbenzyl-substituted salicylic acid derivative composition of claim 5 with a polyvalent metal salt.

12. A polyvalent-metal-modified reaction product of an α-methylbenzyl-substituted salicylic acid derivative composition of claim 7 with a polyvalent metal salt.

13. A polyvalent-metal-modified reaction product of an α-methylbenzyl-substituted salicylic acid derivative composition according to claim 11, wherein the polyvalent metal is calcium magnesium, aluminum, cooper, zinc, tin, barium, cobalt or nickel.

14. A polyvalent-metal-modified reaction product of an α-methylbenzyl-substituted salicylic acid derivative composition according to claim 12, wherein the polyvalent metal is zinc.

15. A polyvalent-metal-modified reaction product of an α-methylbenzyl-substituted salicylic acid derivative composition according to claim 11, wherein $R_1$ is methyl; and wherein $R_2$ $R_3$ are hydrogen atoms and X is a chlorine atom; and wherein the polyvalent metal is zinc.

* * * * *